(12) United States Patent
Gradl

(10) Patent No.: US 7,300,793 B2
(45) Date of Patent: Nov. 27, 2007

(54) METHOD FOR PREVENTING THE ADHESION OF PARTICLES

(75) Inventor: Gabriele Gradl, Berlin (DE)

(73) Assignee: Evotec Technologies GmbH, Dusseldorf (DE)

( * ) Notice: Subject to any disclaimer, the term of this patent is extended or adjusted under 35 U.S.C. 154(b) by 0 days.

(21) Appl. No.: 10/483,218

(22) PCT Filed: Jul. 17, 2002

(86) PCT No.: PCT/EP02/07964

§ 371 (c)(1),
(2), (4) Date: Jan. 8, 2004

(87) PCT Pub. No.: WO03/012077

PCT Pub. Date: Feb. 13, 2003

(65) Prior Publication Data

US 2004/0175354 A1 Sep. 9, 2004

(30) Foreign Application Priority Data

Jul. 27, 2001 (DE) .............................. 101 36 722

(51) Int. Cl.
*C12N 5/00* (2006.01)
(52) U.S. Cl. .................... 435/325; 435/29; 435/30; 435/243; 435/4; 424/77; 514/724
(58) Field of Classification Search ............ 427/2.11; 435/325, 243; 436/8, 18; 424/77
See application file for complete search history.

(56) References Cited

U.S. PATENT DOCUMENTS

| | | | |
|---|---|---|---|
| 5,229,366 A | 7/1993 | Tsukada et al. | |
| 5,241,022 A | 8/1993 | Watanabe et al. | |
| 5,958,443 A | 9/1999 | Viegas et al. | |
| 5,977,252 A | 11/1999 | Wagner et al. | |

2003/0180251 A1  9/2003  Friedrich et al.

FOREIGN PATENT DOCUMENTS

| | | |
|---|---|---|
| DE | 199 12 798 C1 | 2/2000 |
| DE | 101 17 099 A1 | 2/2002 |
| JP | 04 316483 A | 11/1992 |
| JP | 04316483 A * | 11/1992 |
| WO | WO98/47948 A1 | 10/1998 |

OTHER PUBLICATIONS

Adamson et al, "Adaption of Mammalian Cell Lines to High Cell Densities" US Statutory Invention Registration H1532, Published May 7, 1996.*
"Powdered Cell Cultured Media Formulations" Biological Industries, Isreal, http://www.bioind.com/img/formula/r_21.pdf accessed Feb. 9, 2005.*
Hisada, T, "On the Adhesion of Culture Cells to Some Polymers (In Vitro)" Journal of Dental Science and Technology); 1976, vol. 17, No. 38, pp. 91-101. (Japanese Language) Translation provided.*
Holm et al., "High Bovine Blastocyst Development in a Static in vitro Production System using SOFaa Medium Supplemented With Sodium Citrate and MYO-INOSITOL With or Without Serum-Proteins," Theriogenology, 52:683-700, 1999.
Yamada KM. Cell surface interactions with extracellular materials. Annu Rev Biochem. 1983;52:761-99.
Gilges, M. et al., "Capillary Zone Electrophoresis Separations of Basic and Acidic Proteins Using Poly(vinyl alcohol) Coatings in Fused Silica Capillaries", Analytical Chemistry, vol. 66. No. 13, Jul. 1, 1994, pp. 2038-2046.
Gilges et al., "CZE Separations of Basic Proteins at Low pH in Fused Silica Capillaries with Surfaces Modified by Silane Derivatization and/or Adsorption of Polar Polymers", HCR Journal of High Resolution, vol. 15, No. 7, 1992, pp. 452-457.

* cited by examiner

Primary Examiner—Leon B. Lankford, Jr.
Assistant Examiner—Allison M. Ford
(74) Attorney, Agent, or Firm—Caesar, Rivise, Bernstein, Cohen & Pokotilow, Ltd.

(57) ABSTRACT

A method for the prevention of the adhesion of particles, in particular cells and cellular components in solution to surfaces, characterized in that to the solution is added at least one polyalcohol.

4 Claims, 1 Drawing Sheet

Figure
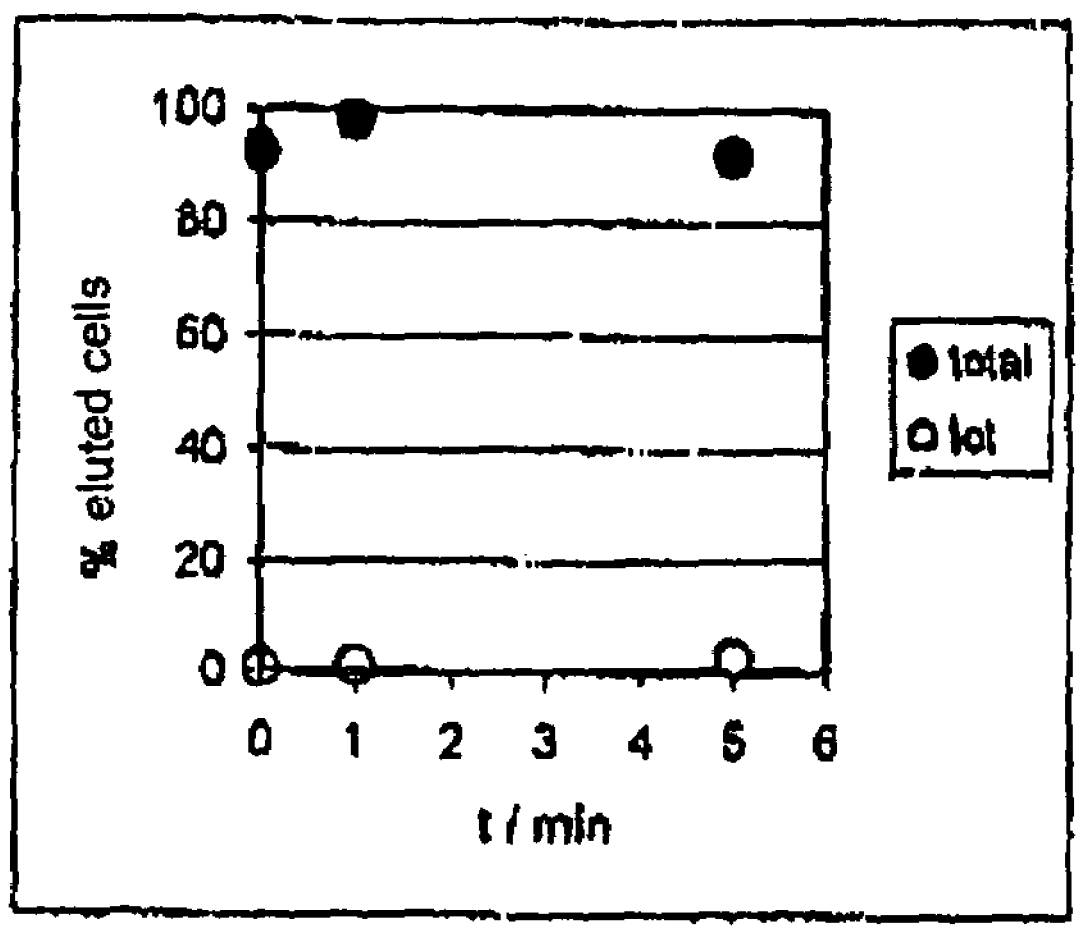

METHOD FOR PREVENTING THE ADHESION OF PARTICLES

The invention relates to a method for the prevention of the adhesion of particles, in particular of cells and cellular components, to surfaces, whereby a polyalcohol is added to the solution which contains the particles.

The adherence to surfaces is a fundamental property of cells. This becomes apparent, for example, in the interaction of cells with an extracellular matrix, which is an important factor in controlling the gene expression or general cell function. These processes are influenced in particular via proteins on the cell surface.

Indeed, this property of cells often presents a big problem during the preparation of cell cultures and the nondestructive examination of cells or cellular components. An adherence of cells to, for example, surfaces of the accessories and containers used in the preparation is undesirable. Technologies for the microanalysis of biological samples in particular can not be utilized for cell examinations without problems. These systems that contain, for example, canal systems like in the "Lab-on-Chip"-technology, often only have dimensions of a few micrometers. Furthermore, the selection of the surface materials to be used of these microanalysis systems is bound to the particular manufacturing process or the material of the microstructures in itself. Microchannel analysis systems, for example, are made from glass, silicon, silicone, and organic polymers, such as PMMA or polyurethane, all substrates that facilitate the adhesion of cells. The surface material consequently can not be freely chosen according to the requirements for a minimal cell adhesion.

In order to prevent cell adherence/adhesion, the surface of the microstructures in itself is therefore modified. Various chemical compounds, in general hydrophobic silanes and hydrophilic polymers (hydrogels) are used for this purpose.

Carlson et al. ((1997): "Self-Sorting of White Blood Cells in a Lattice" in "Physical Review Letters" 79, No. 11, p. 2149-2152) succeeded with the known coatings in the sorting of blood cells, for example, in mechanical microfilter systems. But white blood cells thereby irreversibly adhered to the entrances of microchannels. This is desirable in the described system, but at the same time shows the present limitations in the use of microchannels for the nondestructive examination of cellular samples.

Further investigations by Li et al. ("Transport, Manipulation, and Reaction of Biological Cells On-Chip Using Electrokinetic Effects" in "Analytical Chemistry" (1997) 69, 1564-1568) showed that blood cells can be brought into 40 μm-wide microchannels. But the cells were subsequently lysed with a reagent and only then subjected to an analysis. However, the recovery of eukaryotic, particularly of living mammalian cells, from microchannels makes high demands on the selection of the surface materials of the channels.

Further investigations, for example the coating of glass lamina with polyvinyl alcohol, showed that such a surface modification can minimize an adhesion of mouse fibroblast (Hisada, T. (1976): "The adhesion of culture cells to some polymers" (Japanese language) in "Shika Rikogaku Zasshi" 17(38), p. 91-101)).

It could likewise be shown, that copolymer particles from poly(methyl methacrylate) and polyvinyl alcohol do not adhere to blood cells and are not phagocyted by monocytes and neutrophiles (Ayhan, H. and E. Piskin (1997): "Interaction of activated leukocytes with polymeric microspheres" in "International Journal of Artificial Organs" 20(12), 704-707).

Krylov et al. (in "Electrophoresis", 21, 767-773, 2000) furthermore found, that the adherence of cells to glass or polystyrene is markedly reduced, if the surfaces are modified with hydrophilic polymers (hydrogels) such as polyvinyl alcohol.

However, in all the mentioned investigations, it is necessary to carry out a direct surface coating, whereby, for example, polyvinyl alcohol (PVA) is immobile bound to the surface, that is a surface coating or a copolymerization of a substrate with PVA is carried out. For the implementation of the coating, complicated, in particular to exact temperature specifications bound, multistep and thereby very time-consuming processes are necessary. Furthermore, particularly the coating of surfaces that consist of polymers such as polystyrene is problematic, since this material can be damaged by the temperatures of far above 100° C. that are necessary for the coating. The method can therefore only be satisfyingly applied to the use with glass surfaces.

Furthermore, it is often impossible, in particular due to the only small diameters of the microstructures in microanalysis systems, to achieve a coating that is satisfying. Thus, for example, a uniform distribution of the polymers or other coating materials across the surfaces of the corresponding microstructures, for example of channel structures of a diameter of only a few micrometers, is not or only insufficiently possible.

It is therefore the object of the present invention to develop a method, that independent of the nature and surface properties of a microanalysis system allows an essentially nondestructive and loss-free examination of particles, particularly of cells and cellular components, in solution in these systems.

The object is solved by a method according to claim 1 and a solution according to claim 12.

The method comprises according to the invention the addition of a substance to the solution that contains the particles, particularly cells or cellular components, but also, for example, may contain proteins and peptides, that are present in the free form or bound to structures such as, for example beads. This substance according to the invention causes the adherence of these particles to surfaces, particularly surfaces of a microanalysis system, to be essentially prevented.

In the only figure, a diagram is shown that illustrates the recovery rate of suspended Jurkat cells from a microliter-syringe versus the residence time t in the presence of 0.5% PVA.

According to the invention this substance involves a polyalcohol, in particular polyvinyl alcohol, for example polyvinyl alcohol VA 30,000-70,000 and/or polyglycol, preferably polyethylene glycol. Surprisingly, the addition of this substance to the solution did not show a toxic effect relating to living cells or does not cause change of cellular components. Especially suitable is a concentration of the polyalcohol in solution of 0.01% (w/v) to 5% (w/v). Considering polyvinyl alcohol as an example, it could even be shown, that the anti-adhesion effect of the polyalcohol by far exceeds that of known substances that are used as anti-adhesives (table 3). The water solubility and additional properties, listed below, of the polyalcohol cause a universal applicability in all aqueous particle solutions.

An additional important property of this substance, that in particular qualifies it for the use in solutions which contain cells and/or cellular components, is that it has no influence on the physiologic pH-value of the solution.

Many methods of analysis, that are applied in microanalysis systems, are based upon the recording and evaluation of optical signals, such as, for example, fluorescence correlation spectroscopy, fluorescence resonance energy transfer, fluorescence polarization, fluorescence intensity distribution analysis, or, for example, UV-spectroscopy. Therefore, it was all the more important for the universal applicability of this substance, that it does not influence an optical analysis, i.e. particularly does not show autofluorescence or change the refractive index of the solution. These requirements are very well met by polyalcohols, particularly polyvinyl alcohols or polyglycols.

The method according to the invention now allows an essentially loss-free examination and manipulation, particularly separation, of the particles, particularly in microanalysis systems.

Hereby it may concern microanalysis systems that have, for example, channels with a height of from 1-1,000 μm, particularly 2-500 μm, especially preferred 40 μm; a width of 100-2,000 μm, particularly 200-600 μm, and a length of 100 μm-10 cm, preferably 1-2 cm. The systems may consist in particular of glass, silicon, silicone, organic polymers, or another suitable material. Specific embodiments of the microanalysis systems may also have electrodes, in particular for the generation of dielectric forces for the manipulation of the particles that are to be examined, for example for the microscopic, optical and/or electrical analyzing, for the sorting, separating, electroporating, fusing and separating of the particles, particularly of cells.

Microanalysis systems, for example, thus comprise electrodes as dielectric junctions in the microchannels for the sorting of suspended particles (in particular cells), or in other microanalysis systems the electrodes are arranged in such a way that the cell fusion and/or cell poration can be carried out, and other systems comprise two electrode levels in a closed microchannel, a dielectric field cage in a channel intersection as well as electrodes developed as dielectric junctions for the implementation of a stop-flow analysis as well as a subsequent sorting of the analyzed particles. Whereby, the microchannel systems may also comprise combinations of the various electrode systems.

Even the injection of the particles into such a system, which is often carried out with the help of a plastic or glass syringe, does no longer lead to losses, which are caused by the adherence of the particles to the syringe body.

Since the added substance according to the invention also does not influence a living cell, it is, for example, possible, to directly examine cells, to sort on the basis of the examinations and then to specifically recreate cell cultures with the separated cells. That way, for example, cells with a certain property, for instance with a certain kind of receptors on the cell surface, are specifically and essentially loss-free separated from other cells and multiplied.

The method according to the invention is in general suitable for all cell types, consequently both for eukaryotic cells and for prokaryotic cells.

In table 1, the portion of living cells after the examination and/or manipulation in various microanalysis systems in the presence of polyvinyl alcohol is shown. (Jurkat-cells in Cytocon™ sorter chips (No. 1 and 2), in Cytocon™ porator chips (No. 3-5), and Cytocon™ loader chips (No. 6 and 7)).

TABLE 1

| | Flow Rate in μl/h | | Cell Amount | | Recovery |
|---|---|---|---|---|---|
| No. | Sample | Sheath fluid | Per μl | Total | Rate % |
| 1 | 10 | 288 | 660 | 440 | 84 |
| 2 | 10 | 288 | 132 | 220 | 64 |
| 3 | 10 | 288 | | 689 | 74 |
| 4 | 10 | 144 | | 144 | 100 |
| 5 | 10 | 144 | | 144 | 113 |
| 6 | 18 | 144 | 160 | 160 | 87.3 |
| 7 | 20 | 18 | 305 | 243 | 63 |

In table 2, in each case, the portion of Jurkat-cells and blood cells in the fractions 1 and 2 after a cell separation in a microanalysis system (Cytocon™ chip) is shown.

TABLE 2

| Number of Cells Total | | | Fraction 1 | | | Fraction 2 | | |
|---|---|---|---|---|---|---|---|---|
| Total | Jurkat | RBC | Total | Jurkat | RBC | Total | Jurkat | RBC |
| 6,355 | 161 | 6,194 | 345 | 151 | 194 | 6,010 | 10 | 6000 |
| 100% | 2.5% | 97.5% | 100% | 43.8% | 66.2% | 100% | 0.17% | 99.8% |

The method according to the invention is likewise suitable for cellular components. It has no influence on their structure and does not cause degeneration. Under cellular components are to be understood, for example, liposomes, lipid membranes, lipids, proteins, DNA, nucleic acids, messenger substances, sugar, glycans, and/or glycoproteins. In principle, all components of a cell are thus concerned, but also cell fragments.

The method according to the invention provides, besides the advantage that it prevents an adherence of the particles to the surfaces of microanalysis systems, that may in particular consist of silicon, silicone, glass, and/or organic polymers such as PMMA, polyurethane, polycarbonate, polypropylene, polystyrene, polyethylene, polyvinyl chloride, Teflon®, polyacryl (fiber), nylon®, and/or perlon®, also the possibility that it prevents the adhesion of biomolecules, in particular cells, cell membranes, cellular components such as lipids, proteins (in particular antibodies), DNA, nucleic acids, messenger substances, biotin, sugar, glycans, and/or glycoproteins among one another or to surfaces coated with such molecules.

In table 3, the cell adherence to polystyrene culture dishes in the presence of various substances is shown.

TABLE 3

|  | Jurkat | | U937 | |
| --- | --- | --- | --- | --- |
|  | Adherence | Vitality | Adherence | Vitality |
| RPMI 10% FBS | — | 97% | 9 | 100% |
| PBS | 999 | 99% | 999 | 98% |
| PBS + Ca, Mg | 999 | OK | 999 | OK |
| 0.1% BSA | 99 | OK | 999 | OK |
| 0.5% BSA | — | OK | 99 | OK |
| 1% PVP 15 | 99 | 100% | 999 | 100% |
| 1% PVP 25 | 99 | 100% | 999 | 100% |
| 1% PEG 5,000 | 99 | 100% | 999 | 100% |
| 1% MC 15 | 99 | OK | 999 | OK |
| 1% MC 400 | 99 | OK | 99 | OK |
| 10% Ficoll 70 | 999 | OK | 999 | OK |
| 10% Ficoll 400 | 999 | OK | 999 | OK |
| 10% Dextran T10 | 999 | OK | 999 | OK |
| 1% PVA 30,000–70,000 | — | 97% | (9) | 98% |
| 0.1% PVA 30,000–70,000 | — | OK | (9) | OK |
| 0.01% PVA 30,000–70,000 | — | OK | (9) | OK |

Notes:
— = no adherence
(9) = very low adherence
9 = distinct adherence
99 = strong adherence
999 = very strong adherence
OK = no quantification, but no difference to the control noticeable Whereby within the meaning of this invention by surface is meant any surface, but in particular channel surfaces, surfaces of storage containers of microanalysis systems, tubing, syringes, injection modules, or surfaces of synthetic microparticles.

Furthermore, a solution was found, that in general is suitable for the examination of particles, in particular of cells and cellular components in microanalysis systems. This solution contains saline buffer, in particular PBS, and/or inositol, and polyvinyl alcohol. However, to the solution may also be added other components known in the context of cell solutions such as, for example, magnesium and calcium ions.

The portions of saline buffer, inositol, and/or PVA are variable. The buffer may be diluted in a variable mixing ratio by normoosmolar, hyperosmolar, or hypoosmolar sugar solutions (for instance sucrose or inositol). The portion of saline buffer in the solution may be varied between 0 and almost 100%, whereby portions of 20%, 50%, or almost 100% are especially preferred.

Inositol is preferably used as a 0.2 to 0.5 M solution, for instance of inositol in distilled water, especially preferred a 0.3 M solution. Whereby, the portion of inositol solution and the solution according to the invention may also be varied between 0 and almost 100%. Especially preferred are indeed portions of 50%, 80%, and almost 100%.

Polyvinyl alcohol with a molecular weight of between 30,000 g/mol and 70,000 g/mol is particularly well suited for the solution according to the invention, whereby the amount of PVA in the solution according to the invention lies between 0.1% (w/v) and 1.1% (w/v), preferably between 0.3% (w/v) and 0.6% (w/v), especially preferred between 0.45% (w/v) and 0.55% (w/v).

The solution according to the invention may be utilized independent of type and properties of the particles, in particular for their examination and manipulation in microanalysis systems.

For this purpose, the particles may be directly suspended in this solution and placed in the microanalysis system. However, it is also possible to add this solution to particle suspensions.

EXAMPLE 1

Influence of Polyvinyl Alcohol on the pH-Value of a Solution

The pH value of a 1% solution of polyvinyl alcohol in PBS was measured and lies at 7.31 (the physiologic pH range is pH 7.2-7.4).

EXAMPLE 2

The Influence of Polyvinyl Alcohol on the Cell Adhesion in Comparison to Other Additives Solutions:

Jurkat-cells (clone E6-1 from the European Collection of Animal Cell Cultures, Salisbury, England) and U937-cells (monocytic cell line of the European Collection of Animal Cell Cultures, Salisbury, England) were cultivated in RPMI 1640 medium ((GIBCO Life Technologies, Karlsruhe) by adding 100 IU/ml each of penicillin and streptomycin (Seromed/Biochrom, Berlin) and 10% fetal calf serum (Seromed/Biochrom, Berlin). 3 ml each of the cell suspension were centrifuged off and taken up in 300 μl of phosphate-buffered saline solution without calcium or magnesium (PBS, Seromed/Biochrom, Berlin). The wells of a 24-well plate (24-well polystyrene culture plates, Corning Costar) were each filled with 500 μl PBS by adding the table 3 indicated concentrations of the subsequently listed substances. Methylcellulose (15 and 4,000 centipoise viscosity of a 2% solution, SIGMA Aldrich GmbH, Steinheim), Ficoll 70 and Ficoll 400 (Pharmacia, Uppsala, Sweden), Dextran T10 (Pharmacia, Uppsala, Sweden), polyvinyl pyrrolidone 15 and 25 (Serva), polyethylene glycol 5,000 (Fluka) and polyvinyl alcohol 30,000-70,000 (SIGMA Aldrich GmbH, Steinheim) were tested. 50 μl of the cell suspension described above were added. A sample in 500 μl cell culture medium (in which adherence of these suspension cells does not occur) served as control.

Implementation:

The samples were incubated for 30 minutes at 37° C. The supernatant with non-adhered cells was removed and replaced by buffer. The adherence was qualitatively evaluated (refer to table 3). The cells in both supernatant and the wells were stained with trypanblue solution (0.2%, SIGMA Aldrich GmbH, Steinheim) in order to examine the vitality of the cells. Only polyvinyl alcohol has a very distinct inhibitory effect on the cell adherence with both cell lines. The effect already occurs at a concentration of 0.1% (w/v).

Result:

Many substances, to which an anti-adhesive effect is assigned, were tested in comparison to polyvinyl alcohol. Bovine serum albumin (BSA), for instance, which is known from flow cytometry for the blocking of non-specific bonds and used in immunoreactive detection (e.g. Western blot technique). Furthermore, various hydrophilic polymers that are used in density gradient centrifugation of blood samples or in cell culture techniques were examined. Even the influence of cadherins and integrins, specific cell-cell and cell-substrate adhesion molecules, in buffers without calcium and magnesium were examined. These molecules need calcium for interaction. It became apparent, that polyvinyl alcohol distinctly surpasses the other substances in the effect of successful preventing an adhesion of suspended cells on the sample carrier.

EXAMPLE 3

Examination of the Toxicity of Polyvinyl Alcohol with Respect to Living Mammalian Cells Implementation:

The use of 0.5% (w/v) of PVA for the recovery of cells from a microliter syringe was examined. Jurkat-cells were suspended in a concentration of $5.69 \times 10^5$ cells per ml in PBS with 0.5% PVA (w/v). 5 µl of this suspension were drawn up into a 5 µL-syringe (Dynatech). 1 µl each were transferred immediately and after 1 and 5 minutes, respectively, into a well of a Terasaki plate (NUNC, Wiesbaden). The cells were stained in the plate with the live/dead stain kit (Molecular Probes, Leiden, Netherlands) and counted; thereby their vitality was simultaneously examined. The recovery rate was determined.

Result:

More than 90% of the cells could be recovered—after 5 minutes as well—from the syringe. They therefore had not adhered. The percentage of dead cells initially, thus at 0 minutes, amounted to 0.8% and increased after 5 minutes only to 2.4%.

EXAMPLE 4

Examination of Cells in Microanalysis Systems Using a Cell Buffer with Polyvinyl Alcohol Material:

The use of polyvinyl alcohol for the work with suspended cells in microchannels was examined with a Cytocon™ 300 device system. The Cytocon™ chips consist of glass and exhibit channels with a height of 40 µm, a width of 200-600 µm, and a length of about 1-2 cm, whereby specific embodiments of the chips may also exhibit electrodes in the channels. Cytocon™ sorter chips comprise, for example, electrodes as dielectric junctions in the microchannels for the sorting of the suspended particles (in particular cells), in Cytocon™ porator chips the electrodes are arranged in such a way, that cell fusion and/or cell poration can be carried out, and Cytocon™ loader chips, that exhibit two electrode levels in a closed microchannel, a dielectric field cage in a channel intersection, as well as electrodes developed as dielectric junctions, are suitable for the performance of a stop-flow analysis as well as the subsequent sorting of the analyzed particles.

Polyvinyl alcohol with a molecular weight of 30,000 g/mol to 70,000 g/mol was used. The polyvinyl alcohol was dissolved in the buffer to 0.5% (w/v) and was present during the entire manipulation of the cells in the microchannels.

Implementation:

The cells were suspended in the buffer and injected into a Cytocon™ chip. The suspension was transported within the channel system with a certain flow rate ("sample") and at the chip exit accelerated with a sheath fluid. The rinsed out cells were counted and the recovery rate calculated from the initial concentration and the injected sample amount.

Result:

Even though the cell amount used was only a few hundred cells and the flow rate in the microchannels was very slow (dwell time of the cells in the microchannel about 2 minutes), the recovery rate of cells was very high (table 1) and values around 100% were achievable.

EXAMPLE 5

Fractionation of Blood Cells (Separation of Lyphocytes from Red Blood Cells)

Implementation:

A mixture of whole human blood, Jurkat T-lymphoma cells, and a PVA-containing buffer was prepared. The buffer contained 20% (v/v) PBS, 80% (v/v) 0.3 M inositol solution, and 0.5% (w/v) PVA (30,000-70,000, Sigma). For a better visualization during the experiment, the Jurkat cells were labeled with 10 µM Calcein-AM™ (Molecular Probes).

The blood and the lymphoma cells were diluted as follows: The cell samples were mixed to concentrations of $2.5 \cdot 10^6$ Jurkat cells/ml and $1.8 \cdot 10^7$ red blood cells/ml. Samples of 0.3 µl were injected into a Cytocon™ chip (microanalysis system).

The Cytocon™ chips used for this experiment consisted of glass and exhibited channels with a height of 40 µm, a width of 200-600 µm, and a length of about 1-2 cm. Additionally, the microanalysis system used here, comprised electrodes in one or several microchannels, that are arranged here as dielectric junction for the sorting of the cells.

The cells were separated based on differences in their size and their dielectric properties via the so-called switch electrode (junction) of the Cytocon™ microanalysis system at a frequency of the electric field of 800 kHz and an amplitude of 3-6 V rms at a flow rate of 62-240 µm/s. Under these conditions, the Jurkat cells were deflected and collected in fraction 1, while the red blood cells (RBC) could pass the junction and were collected in fraction 2.

Jurkat cells and red blood cells (RBC) were counted in both fractions in order to be able to determine the accumulation and the yield.

Result:

The accumulation factor for the Jurkat cells in fraction 1 is in an exemplary experiment 17.5. The yield of Jurkat cells in this fraction was 93% in this case (table 2).

Overall (fractions 1 and 2), the cell recovery rate was almost 100%.

The invention claimed is:

1. A method for inhibiting adhesion of particles to surfaces, said method comprising:
   providing the particles comprising at least one of eukaryotic cells, prokaryotic cells, and cellular components thereof;
   providing a substrate comprising a microanalysis system or synthetic microparticles, wherein the substrate has surfaces to which the particles are capable of adhering;
   providing the particles in a solution comprising polyvinyl alcohol; and
   contacting the substrate with the solution, wherein the polyvinyl alcohol is present as a solute in the solution in an amount effective to inhibit adhesion of the particles to the surfaces, wherein the concentration of the polyvinyl alcohol in solution is 0.01% (w/v) to 5% (w/v).

2. A method for inhibiting adhesion of particles to surfaces, said method comprising:
   providing the particles comprising at least one of viable eukaryotic cells and viable prokaryotic cells;

providing a substrate comprising a microanalysis system or synthetic microparticles, wherein the substrate has surfaces to which the particles are capable of adhering;

providing the particles in a solution comprising polyvinyl alcohol; and contacting the substrate with the solution, wherein the polyvinyl alcohol is present as a solute in the solution in an amount effective to inhibit adhesion of the particles to the surfaces;

wherein the concentration of the polyvinyl alcohol in solution is 0.01% (w/v) to 5% (w/v); and wherein the cells retain their viability.

3. The method according to claim 1, wherein the surfaces comprise channel surfaces of the microanalysis system.

4. The method according to claim 1, wherein the surfaces comprise surfaces of the synthetic microparticles.

* * * * *

UNITED STATES PATENT AND TRADEMARK OFFICE
CERTIFICATE OF CORRECTION

PATENT NO. : 7,300,793 B2  Page 1 of 1
APPLICATION NO. : 10/483218
DATED : November 27, 2007
INVENTOR(S) : Gradl It is certified that error appears in the above-identified patent and that said Letters Patent is hereby corrected as shown below:

At column 8, line 48, delete claims 1 through 4 and insert—

--1. A method for inhibiting adhesion of particles to surfaces, said method comprising:
providing the particles comprising at least one of viable eukaryotic cells and viable prokaryotic cells;
providing a substrate comprising a microanalysis system or synthetic microparticles, wherein the substrate has surfaces to which the particles are capable of adhering;
providing the particles in a solution comprising polyvinyl alcohol; and
contacting the substrate with the solution, wherein the polyvinyl alcohol is present as a solute in the solution in an amount effective to inhibit adhesion of the particles to the surfaces;
wherein the concentration of the polyvinyl alcohol in solution is 0.01% (w/v) to 5 % (w/v); and
wherein the cells retain their viability.

2. The method according to claim 1, wherein the polyvinyl alcohol is water-soluble.

3. The method according to claim 1, wherein the surfaces comprise channel surfaces of the microanalysis system.

4. The method according to claim 1, wherein the surfaces comprise surfaces of the synthetic microparticles.--

Signed and Sealed this

Sixteenth Day of November, 2010

David J. Kappos
*Director of the United States Patent and Trademark Office*